United States Patent [19]

Dunn et al.

[11] Patent Number: 4,542,743
[45] Date of Patent: Sep. 24, 1985

[54] VASCULAR CLAMP

[75] Inventors: David C. Dunn, Cambridge; David Scarrow, Somerset, both of England

[73] Assignee: DRG (UK) Ltd., Bristol, England

[21] Appl. No.: 517,931

[22] Filed: Jul. 28, 1983

Related U.S. Application Data

[63] Continuation of Ser. No. 262,667, May 11, 1981, abandoned.

[30] Foreign Application Priority Data

May 14, 1980 [GB] United Kingdom ............... 8015978

[51] Int. Cl.⁴ ............................................. A61B 17/12
[52] U.S. Cl. .................................. 128/327; 128/325; 128/326; 128/346
[58] Field of Search .............. 128/327, 325, DIG. 25, 128/346, 686

[56] References Cited

U.S. PATENT DOCUMENTS

| 2,511,269 | 6/1950 | Jones | 128/327 |
|---|---|---|---|
| 2,756,753 | 7/1956 | Means | 128/327 X |
| 3,156,243 | 11/1964 | Sculley | 128/327 |
| 3,993,076 | 11/1976 | Fogarty | 128/327 X |

FOREIGN PATENT DOCUMENTS

| 1268034 | 3/1972 | United Kingdom | 128/327 |
|---|---|---|---|
| 2053690 | 2/1981 | United Kingdom | 128/325 |

OTHER PUBLICATIONS

Timm et al., "Intermittent Occlusion System", IEEE Trans. on Bio-Med. Engnerg., (Oct. 1970), p. 352.

Primary Examiner—Michael H. Thaler
Attorney, Agent, or Firm—Larson and Taylor

[57] ABSTRACT

A clamp for closing blood vessels and the like is a tapered flat envelope of impermeable plastics film with an inlet tube at its wider end for inflating the envelope and a transverse seal limiting the inflatable region. The other end is tapered and is non-inflatable. It can be tucked under a transverse strip to secure the clamp on a blood vessel. The envelope is widened under the transverse strip and also at the transverse seal to hold the narrow end in place under the strip.

6 Claims, 1 Drawing Figure

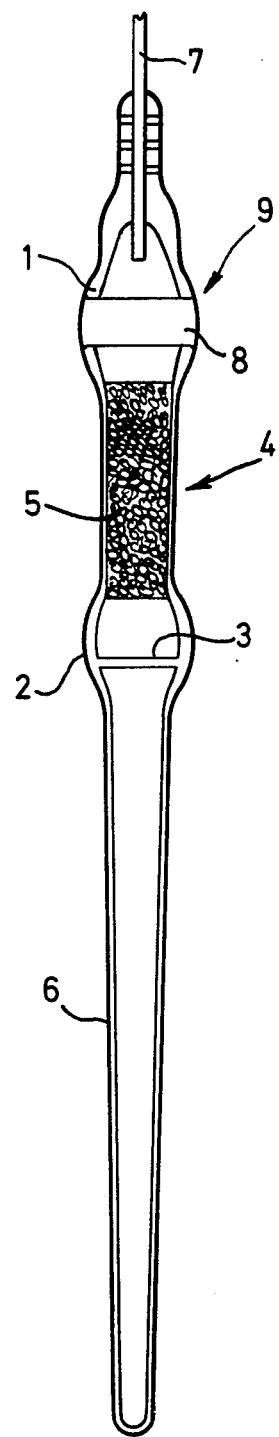

VASCULAR CLAMP

This is a continuation of application Ser. No. 262,667, filed May 11, 1981 now abandoned.

BACKGROUND OF THE PRESENT INVENTION

This invention relates to clamps for clamping blood vessels and other biological vessels having flexible walls, generally as disclosed in my British Patent No. 1,268,034.

The vascular clamp particularly disclosed in Patent Specification No. 1,268,034, although satisfactory in principle, has certain practical inconveniences. The object of the present invention is to eliminate such inconveniences, and in particular to provide a vascular clamp of the kind set forth in Specification No. 1,268,034, that will remain firmly in place.

SUMMARY OF THE PRESENT INVENTION

According to the present invention, a vascular clamp comprises an elongate hollow body in the form of a flat envelope of impermeable flexible sheet material, which can be curved to embrace a vessel to be clamped, and an inlet tube at one end of the envelope for inflation of the envelope to clamp a vessel embraced by the envelope, the envelope having adjacent to the said end a transverse strip of material secured to the edges of the envelope to provide a slot between itself and the envelope through which the other end portion of the body can be threaded, and having spaced from the said strip towards the other end of the envelope a locally wider region, adapted to be threaded through the said slot and to resist unthreading.

The body has a transverse seal between its ends, preferably in the said wider region, so that the end portion remote from the inlet tube does not communicate with the latter and is not inflatable.

Preferably, a locally wider region is also provided at the transverse strip.

BRIEF DESCRIPTION OF THE DRAWINGS

The drawing illustrates a schematic cutaway view of an example of a vascular clamp embodying the present invention.

DETAILED DESCRIPTION OF THE PREFERRED EMBODIMENT

The vascular clamp embodying the invention shown in the accompanying drawing includes a body 4 made of two sheets of flexible plastics film sealed together at their edges to form an envelope. This body is tapered and at its wider end an inlet tube 7 is sealed into it, communicating with the space in the envelope between the two layers of plastics film. A transverse seal 3 extends across the body, a few centimetres from the wider end. The internal space of the envelope between the wider end and the transverse seal 3 forms an inflatable balloon. The outer sheet is slightly thicker than the inner sheet so that when the balloon is inflated it will expand primarily on its inner side (this being the side visible in the drawing). The tapering narrower end portion of the envelope is not inflatable and may consist of only a single layer of plastics film.

Near the wider end of the envelope, a strip 8 of the same plastics film material is fastened to the edges of the envelope, which in this region is locally widened to form wings 1.

In the region of the transverse seal 3, the envelope is locally widened to form wings 2. Between the transverse strip 8 and the transverse seal 3, a layer 5 of resilient material, for example plastics foam, is attached to the thinner, inner, face of the envelope.

In use, the clamp is wrapped round a blood vessel or other vessel to be clamped, with the resilient layer 5 adjacent to the vessel, and the narrow tail portion 6 is threaded between the strip 8 and the body, with the wings 2 being pulled through the slot formed by the strip 8. The envelope is then inflated through the inlet tube 7, for example by means of a syringe. This causes the vessel to be occluded. The inlet tube is then closed for example by a tap or clip.

The overall width of the wings 2 is no less than, and preferably slightly greater than, the width of the slot formed by the strip 8, so that the wings 2 will not accidentally slip back under the strip 8 but conversely are not unduly difficult to thread under the strip.

In the absence of the wings 2, there is a tendency for the tail of the vascular clamp to slip from under the strap 8, at least when the clamp is not inflated, so that the user has to check the tightness of the clamp and possibly retighten it after application to a vessel. It is readily apparent that unnoticed slackening could be extremely dangerous during a surgical operation. The wings 2 completely eliminate any tendency of the vascular clamp to slacken after application to a vessel. A further advantage of the wings 2 is that they enable the user to see easily when the correct length of the tail of the clamp has been pulled through the slot under the strip 8. This makes the clamp much simpler to use. In the absence of this facility, it can be very difficult for a surgeon to know when a sufficient length of the tail has been pulled through the slot under the strip 8.

While the clamp is inflated, it is almost impossible for the wings 2 to pass under the strip 8. When the clamp is deflated, the wings pass easily under the strip 8.

I claim:

1. A vascular clamp for occluding a single blood vessel or the like during surgery, said vascular clamp comprising:

an elongated hollow body in the form of a flat envelope of impermeable flexible sheet material, which can be curved to embrace said blood vessel intended to be occluded by said vascular clamp;

an inlet tube at one end of said envelope for selective inflation of the envelope to occlude said vessel embraced by said envelope;

a transverse strip of material secured to the edges of said envelope spaced a predetermined distance from said one end such as to provide a slot between said strip and said envelope through which the other end portion of the body remote from said one end can be threaded;

a first locally wider region of said envelope disposed intermediate said strip and said other end of the envelope, said locally wider region being adapted to be selectively threaded through said slot and to resist unthreading of said other end through said slot, the envelope on the said of said first locally wider region remote from said one end being tapered so that its width reduces in the direction of said other end;

and wherein said envelope has a second locally wider region at said transverse strip.

2. The vascular clamp of claim 1 further comprising a transverse seal between the ends of the body preventing communication between the inlet tube and the end portion of the body remote therefrom.

3. The vascular clamp of claim 1 wherein the envelope is formed from superimposed layers of plastics film material peripherally sealed together, the peripheral seal following the outline of said first locally wider region so that the inflatable portion of the envelope is also of increased width in said first locally wider region.

4. The vascular clamp of claim 1 wherein the envelope is formed from superimposed layers of plastics film material peripherally sealed together, the transverse strip being welded at its ends to the envelope coincidentally with the peripheral seal within the region of said second locally wider region.

5. The vascular clamp of claim 4 wherein said peripheral seal follows the outline of said second locally wider region so that the inflatable portion of the envelope is also of increased width in said second locally wider region.

6. The vascular clamp of claim 1 wherein the envelope has a portion of foam material on the same side thereof as said strip and between the strip and said first locally wider region.

* * * * *